US00PP34658P2

(12) United States Plant Patent
Fouillet

(10) Patent No.: US PP34,658 P2
(45) Date of Patent: Oct. 18, 2022

(54) APPLE TREE NAMED 'R204'

(50) Latin Name: *Malus domestica*
Varietal Denomination: R204

(71) Applicant: IFO S.A.R.L., Seiches-sur-le-Loir (FR)

(72) Inventor: Valérie Fouillet, Saint Sylvain d'Anjou (FR)

(73) Assignee: IFO S.A.R.L., Seiches sur le Loir (FR)

( * ) Notice: Subject to any disclaimer, the term of this patent is extended or adjusted under 35 U.S.C. 154(b) by 0 days.

(21) Appl. No.: 17/803,054

(22) Filed: Jan. 25, 2022

(30) Foreign Application Priority Data

Jul. 9, 2021 (FR) ..... 21174

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

'R204' is a new apple tree notable for its fruit, which exhibits attractive red and pale yellow-orange flesh, stores well and is well-suited for the fresh market.

6 Drawing Sheets

Latin name: *Malus domestica.*
Variety denomination: 'R204'.

BACKGROUND OF THE VARIETY

'R204' is a new and distinct variety of apple tree (*Malus domestica*) obtained from a controlled cross of female parent 'Honeycrisp' (U.S. Plant Pat. No. 7,197, expired) x 'CR35-1' (male parent, not patented) carried out at Seiches-sur-le-Loir, France in 2009. Seeds obtained from the cross were planted at Seiches-sur-le-Loir, and 'R204' was selected from the resulting seedlings for propagation and further observation. 'R204' was first asexually propagated by grafting at Seiches-sur-le-Loir in 2014, and has since been observed to remain true to type through successive asexually propagated generations.

BRIEF DESCRIPTION OF THE VARIETY

The 'R204' apple tree is distinguished by its fruit, which exhibits attractive red and pale yellow-orange flesh and is well-suited for fresh consumption. Comparisons of 'R204' to its parents and to similar variety 'R201' (U.S. Plant Pat. No. 28,218) are shown in Tables 1, 2 and 3 below.

TABLE 1

Comparison of 'R204' to Female Parent 'Honeycrisp'

| Characteristic | 'R204' | 'Honeycrisp' |
|---|---|---|
| Flesh color | Red 50B and pale yellow-orange 19D | Pale orange-white 159D |
| Pattern of over color | Flush and mottled | Solid flush with strongly defined stripes |
| Flesh texture | Moderately crisp, somewhat granular | Extremely crisp |

TABLE 1-continued

Comparison of 'R204' to Female Parent 'Honeycrisp'

| Characteristic | 'R204' | 'Honeycrisp' |
|---|---|---|
| Flavor | Balanced acid and sweetness | Sweet, sub-acid |
| Tree vigor | Moderate | Weak |

TABLE 2

Comparison of 'R204' to Male Parent 'CR35-1'

| Characteristic | 'R204' | 'CR35-1' |
|---|---|---|
| Intensity of red color of flesh | Less intense | More intense |
| Fruit shape | Cylindrical waisted | Globose |
| Russet on cheeks | Absent | Present |
| Fruit size | Medium to large | Small to medium |
| Storageability | Up to about 4 months | Up to about 3 months |

TABLE 3

Comparison of 'R204' to Similar Variety 'R201'

| Characteristic | 'R204' | 'R201' |
|---|---|---|
| Bark color | Grey-brown 199A over greyed-orange 166A | Brown N200C |
| Diameter of fully open flower | 36 mm | 50 mm |
| Date of full bloom | Apr. 19 (2021) | Apr. 24 (2021) |
| Fruit weight | 192 g | 218 g |
| Russet around stalk cavity | Absent | Present |

BRIEF DESCRIPTION OF THE PHOTOGRAPHS

The accompanying photographs were obtained in 2019 and 2020 at Seiches-sur-le-Loir, France. The trees depicted were planted in 2015.

DETAILED BOTANICAL DESCRIPTION OF THE VARIETY

Figure 1:
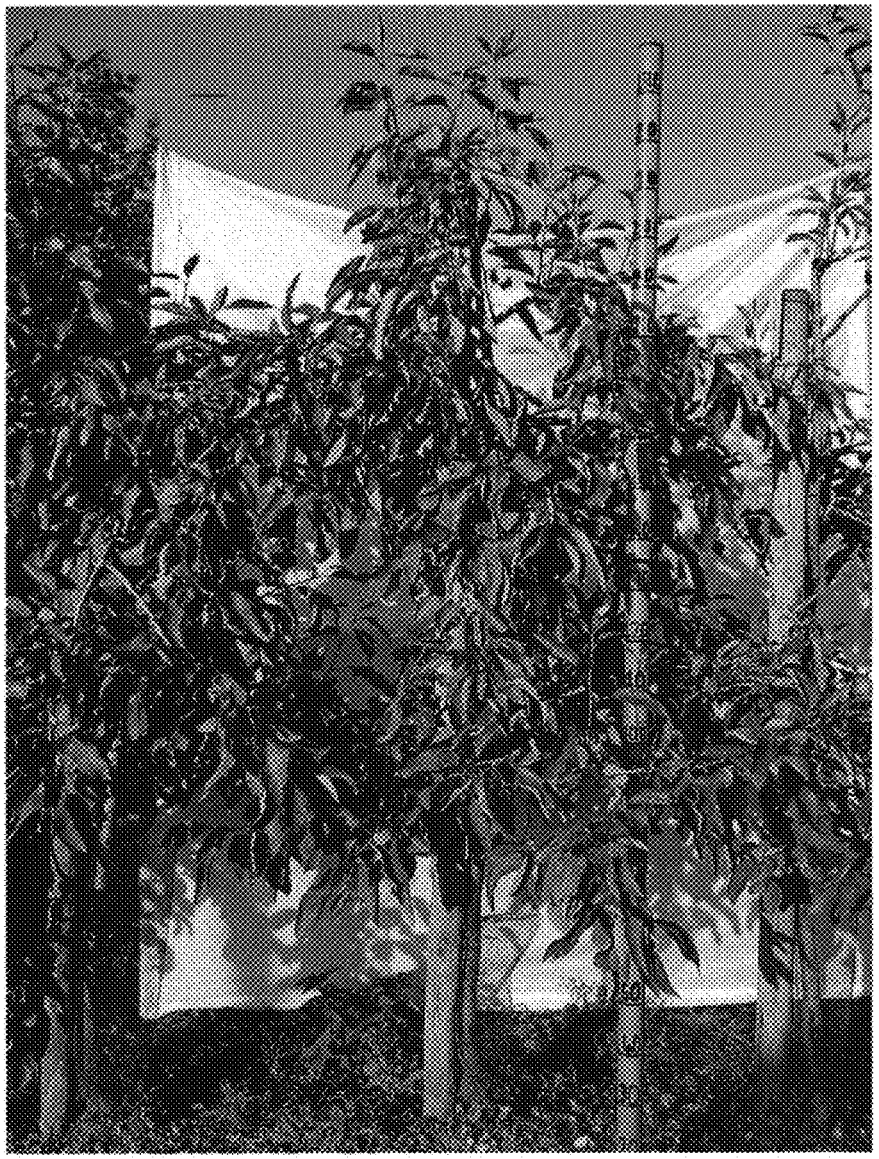
FIG. 1 is a photograph of a 'R204' apple tree with leaves and fruit.
Figure 2:
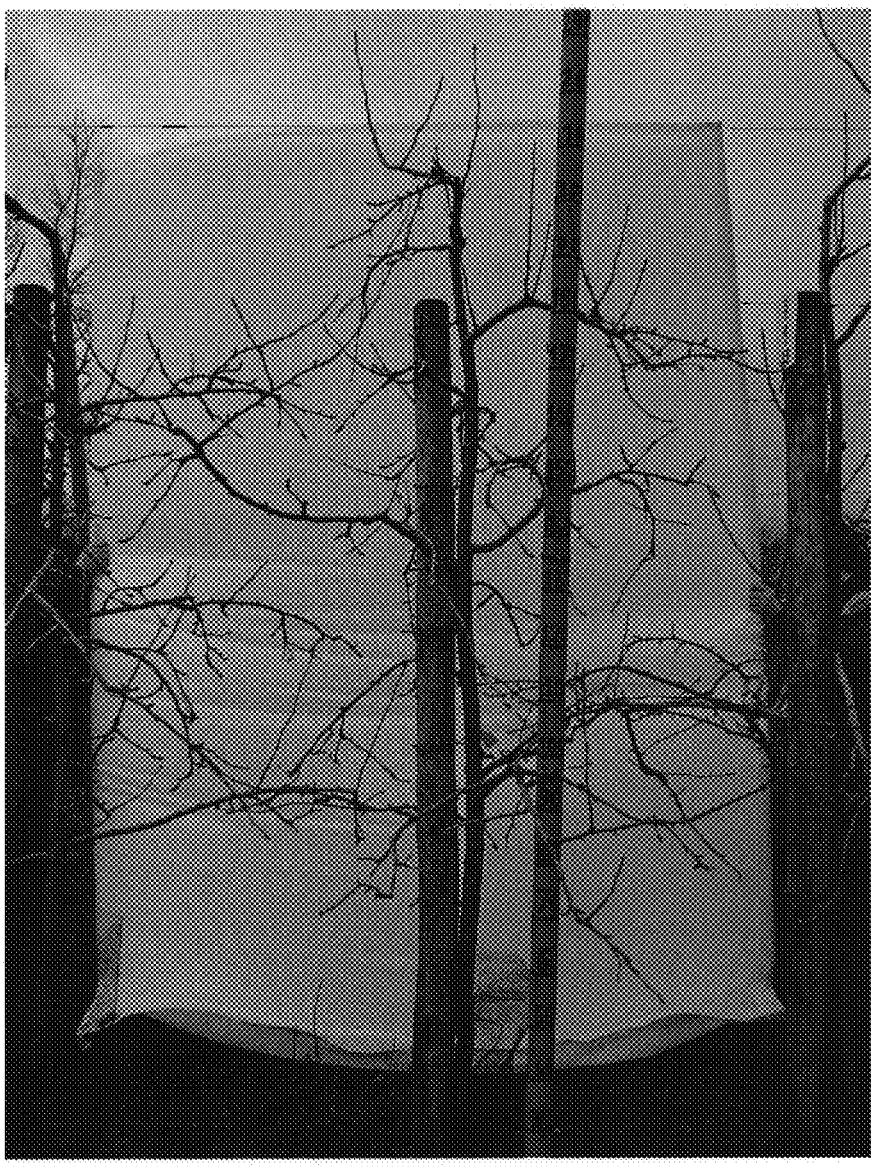
FIG. 2 is a photograph of a 'R204' apple tree without leaves or fruit.
Figure 3:
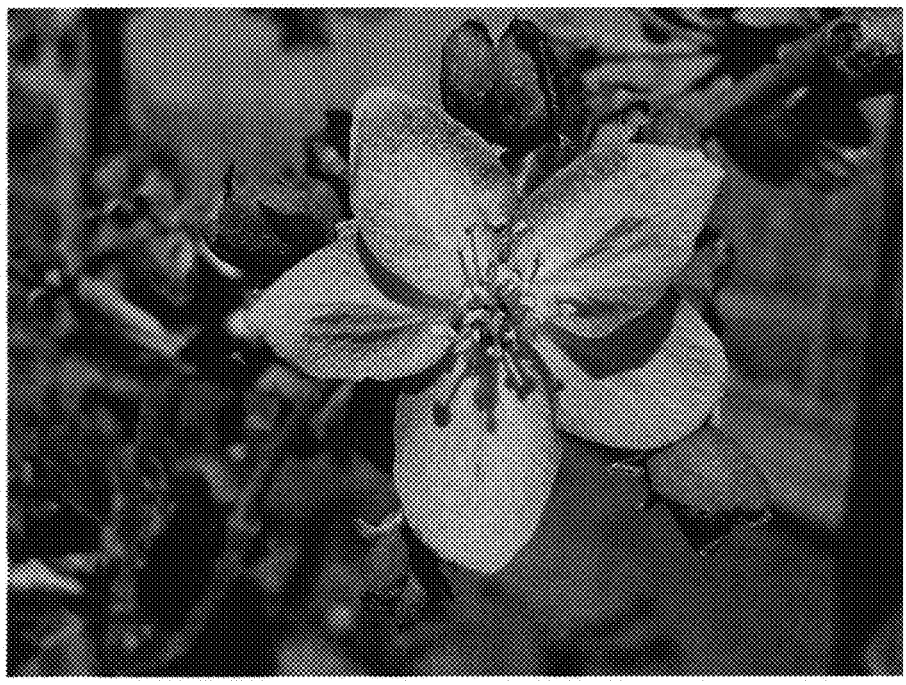
FIG. 3 is a photograph of a blossom and flower buds on a 'R204' apple tree.
Figure 4:
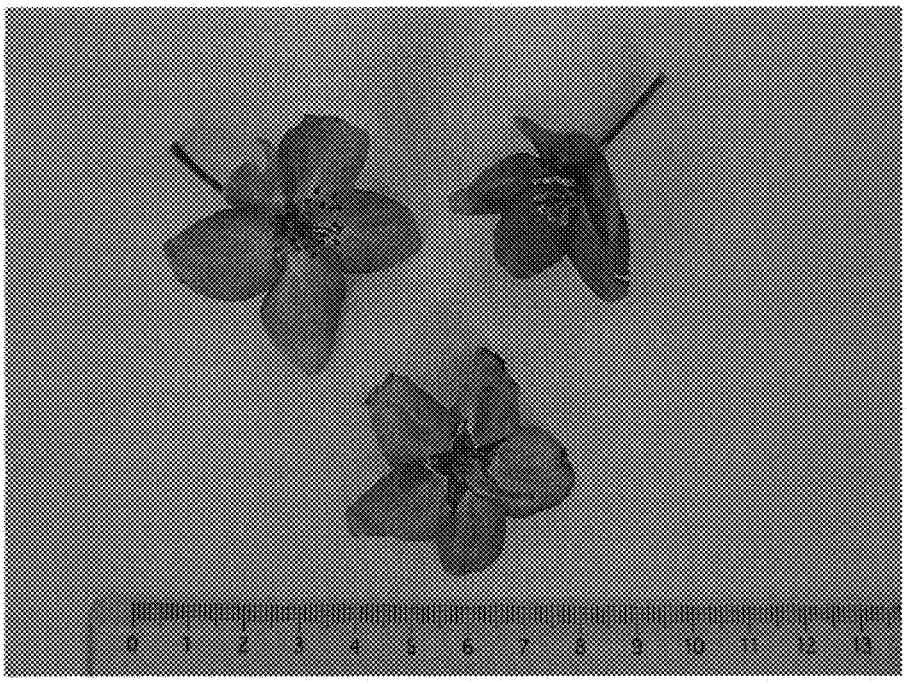
FIG. 4 is a photograph of blossoms from a 'R204' apple tree.
Figure 5:
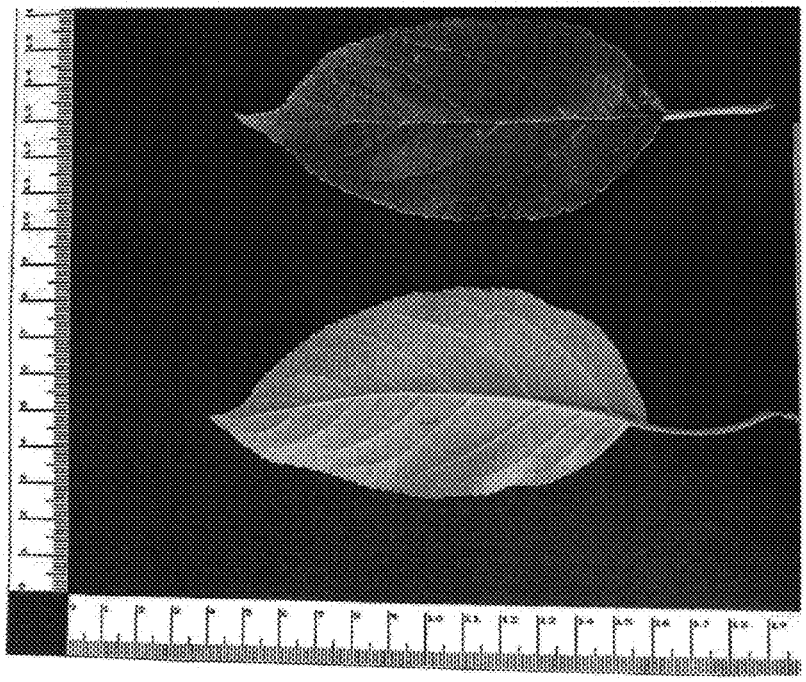
FIG. 5 is a photograph of leaves from a 'R204' apple tree.
Figure 6:
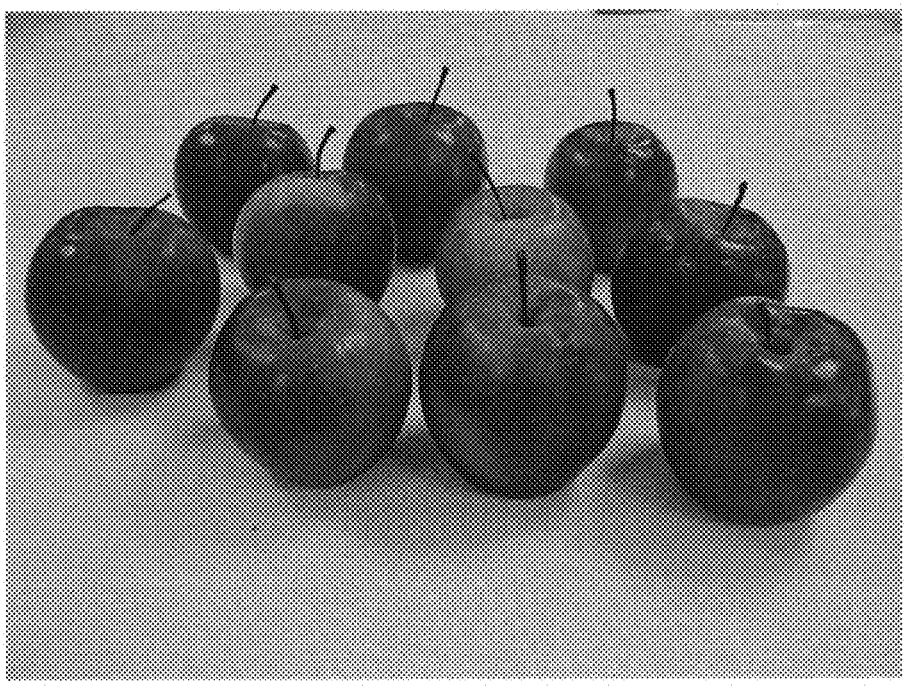
FIG. 6 is a photograph of a stem-end view of apples from a 'R204' apple tree.
Figure 7:
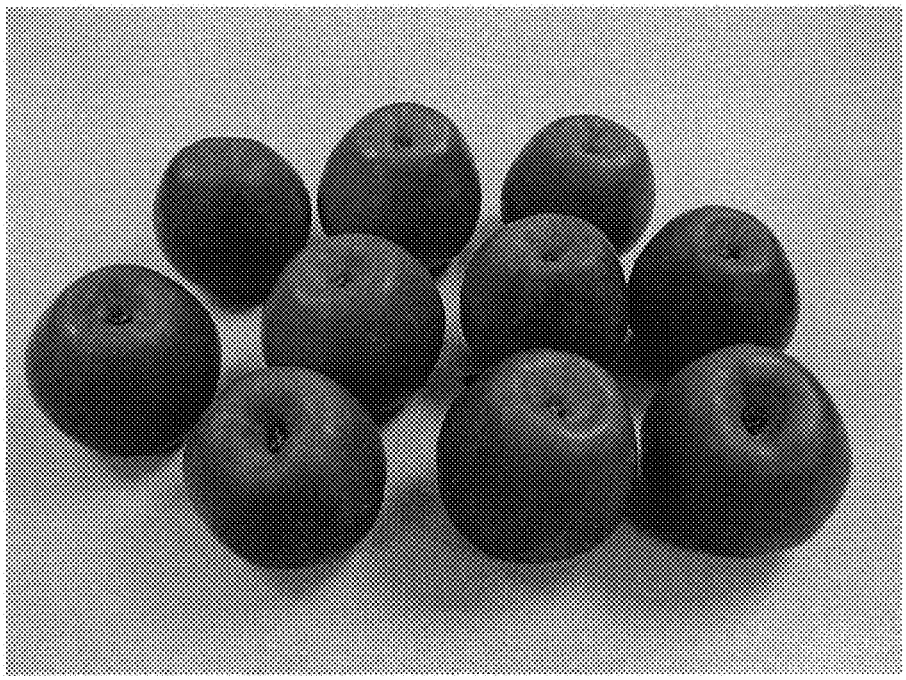
FIG. 7 is a photograph of a calyx-end view of apples from a 'R204' apple tree.
Figure 8:
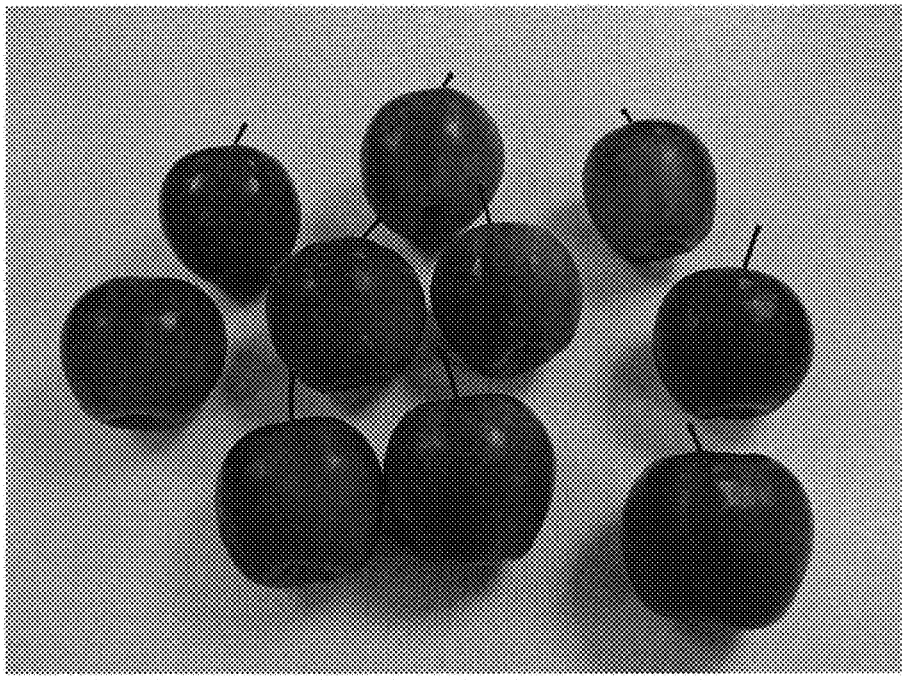
FIG. 8 is a photograph of a side view of apples from a 'R204' apple tree.
Figure 9:
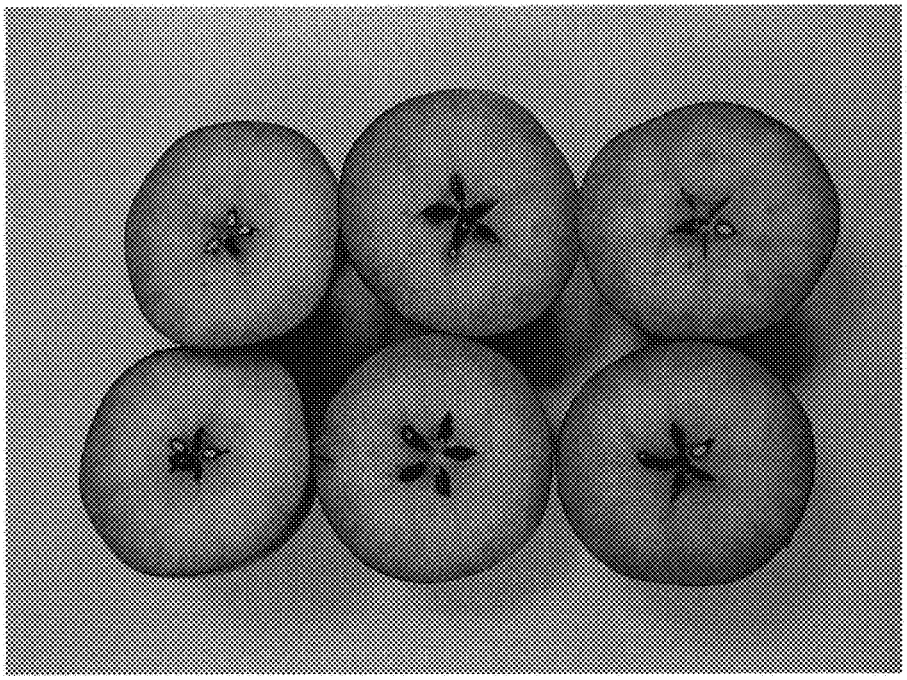
FIG. 9 is a photograph of sectioned apples from an 'R204' apple tree.
Figure 10:
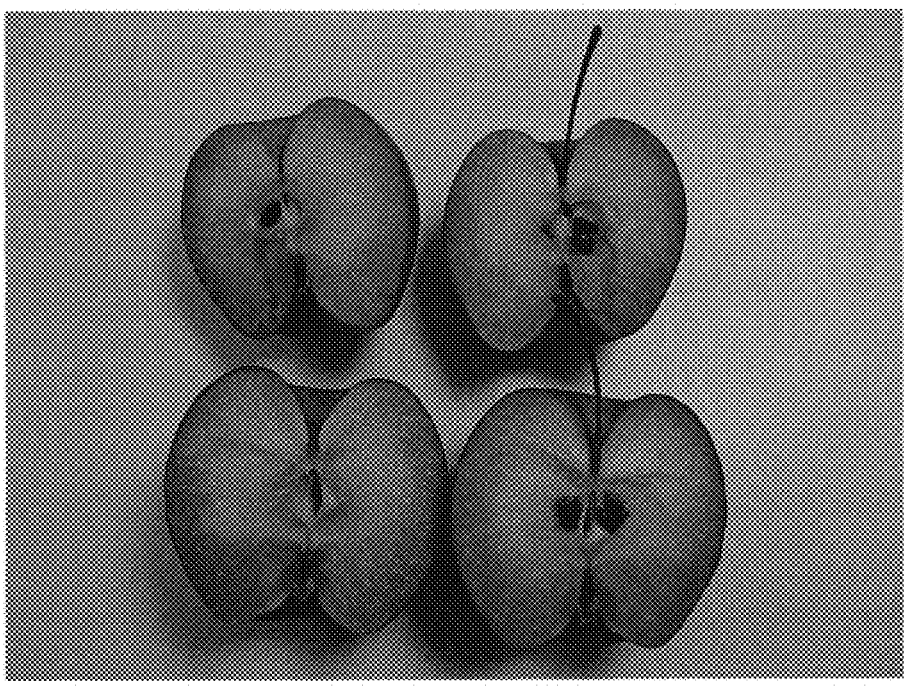
FIG. 10 is a photograph of sectioned apples from a 'R204' apple tree.

The following detailed botanical description was recorded at Seiches-sur-le-Loir, France during the 2019 and 2020 growing seasons (unless otherwise noted). The described trees were planted in 2015 and grown on Pajam®2 'Cepiland' (U.S. Plant Pat. No. 7,715) rootstock. All colors are described with reference to The Royal Horticultural Society Colour Chart ($6^{th}$ ed. 2015, reprinted 2019). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Low to medium.
- *Type*.—Ramified.
- *Habit*.—Spreading.
- *Bearing*.—On shoots and spurs.
- *Spread of mature tree*.—1.4 meters.
- *Height*.—2.0 m.
- *Trunk diameter* (*at* 30 *cm above the graft*).—32 mm.
- *Bark texture*.—Rough.
- *Bark color*.—Grey-brown 199A over greyed-orange 166A.
- *Lenticel length*.—4 mm.
- *Lenticel width*.—1.5 mm.
- *Lenticel height*.—0.5 mm.
- *Lenticel shape*.—Oblong.
- *Lenticel color*.—Yellow-orange 20B.
- *Lenticel density*.—4 per $cm^2$.

Branch (fruiting branches located at about 1 m above the graft union):
- *Length*.—80 cm.
- *Diameter*.—14 mm.
- *Crotch angle*.—80°.
- *Bark color*.—Brown N200C.
- *Lenticel length*.—1.5 mm.
- *Lenticel width*.—1.0 mm.
- *Lenticel height*.—0.3 mm.
- *Lenticel shape*.—Oblong.
- *Lenticel color*.—Greyed-orange 163B.
- *Lenticel density*.—7 per $cm^2$.

One year old shoot:
- *Length*.—15 cm.
- *Diameter*.—3.2 mm.
- *Color*.—Greyed-orange 166A.
- *Pubescence*.—Low.
- *Internode length*.—32 mm.
- *Lenticel length*.—1.0 mm to 1.5 mm.
- *Lenticel width*.—1.0 mm.
- *Lenticel height*.—0.3 mm.
- *Lenticel shape*.—Round to oblong.
- *Lenticel color*.—Yellow-white 158A.
- *Lenticel density*.—10 per $cm^2$.
- *Color of vegetative buds*.—Greyed-orange 166A.
- *Shape of vegetative bud apex*.—Pointed.
- *Position of vegetative buds in relation to shoots*.—Adpressed.

Flower buds (described at balloon stage):
- *Quantity per spur*.—5.
- *Bud shape*.—Round.
- *Apex shape*.—Round.
- *Length*.—9.8 mm.
- *Diameter*.—7.0 mm.
- *Color*.—Red 53C.

Flowers:
- *Inflorescence type*.—Umbel.
- *Diameter of fully open flower*.—36 mm.
- *Depth of fully open flower*.—10 mm.
- *Relative position of petal margin*.—Touching to free.
- *Number per cluster*.—Average 5.
- *Fragrance*.—Very fragrant.
- *Date of first bloom*.—Apr. 18, 2021.
- *Date of full bloom*.—Apr. 19, 2021.
- *Pollination requirement*.—Most varieties with similar bloom date.

Petals:
- *Number per flower*.—5.
- *Petal shape*.—Elliptic.
- *Length*.—19 mm.
- *Width*.—14 mm.
- *Apex shape*.—Rounded.
- *Base shape*.—Rounded.
- *Margin*.—Entire.
- *Color of upper surface*.—Red-purple 61C.
- *Color of lower surface*.—Red-purple 73A.
- *Texture of upper surface*.—Smooth.
- *Texture of lower surface*.—Smooth.

Pistils:
- *Quantity*.—8.
- *Length*.—11.5 mm.
- *Color*.—Greyed-orange 166C with greyed-orange 163B.

Stigma:
- *Diameter*.—0.5 mm.
- *Color*.—Greyed-orange 163B.

Style:
- *Length*.—8.5 mm.
- *Color*.—Greyed-orange 166C.

Ovary:
*Length.*—2.5 mm.
*Diameter.*—1 mm.
*Color.*—Red-purple 70C with green 137C.
Anthers:
*Quantity.*—18 to 20.
*Anther length.*—2 mm.
*Anther width.*—1 mm.
*Color of anther.*—Yellow-orange 20B.
*Pollen presence.*—Present in moderate quantity.
*Pollen color.*—Yellow 8C.
*Position relative to stigma.*—Same.
Pedicel:
*Length.*—15 mm.
*Diameter.*—1.2 mm.
*Color.*—Greyed-orange 166A.
*Pubescence.*—Strongly pubescent, white N155A.
Sepals:
*Quantity.*—5.
*Color of upper surface.*—Greyed-green 194A.
*Color of lower surface.*—Greyed-purple 183A.
*Pubescence.*—Both surfaces strongly pubescent, white N155A.
*Sepal shape.*—Broad triangular.
*Apex shape.*—Acute.
*Margin* (*smooth, serrated, etc.*).—Entire.
*Attitude in relation to corolla.*—Curved downward.
Leaves:
*Shape.*—Elliptic.
*Length.*—119.6 mm.
*Width.*—54.4 mm.
*Length to width ratio.*—2.2.
*Blade margin.*—Crenate.
*Apex.*—Acute with broad long acuminate tip.
*Base shape.*—Acute, wedge-shaped with convex sides.
*Leaf color.*—Upper surface — Green 137A.
*Leaf color.*—Lower surface — Greyed-green 194A.
*Pubescence.*—None on upper surface; weakly pubescent on lower surface.
*Arrangement.*—Alternate.
*Attitude in relation to shoot.*—Outward to downward.
Petiole:
*Length.*—33.1 mm.
*Diameter.*—2 mm.
*Color.*—Red 53A with greyed-purple 187A at base.
Stipules:
*Shape.*—Very elongated obtrullate.
*Length.*—0.9 mm.
*Width.*—0.4 mm.
*Color.*—Greyed-purple 185C.
Fruit:
*Quantity per cluster.*—5.
*Diameter.*—77 mm.
*Height.*—69 mm.
*Height to width.*—0.9.
*Weight.*—192 g.
*General shape in profile.*—Cylindrical waisted.
*Position of maximum diameter.*—Just above equator.
*Ribbing.*—Moderate.
*Crowning at calyx end.*—Moderate.
*Bloom of skin.*—Moderate.
*Greasiness of skin.*—Moderate.
*Background color of skin.*—Red 36D at harvest; red 37A after storage.
*Over color of skin.*—Red N45A at harvest; red 53A after storage.
*Amount of over color.*—85%.
*Intensity of over color.*—Moderate to intense.
*Pattern of over color.*—Flushed and mottled.
*Fruit lenticel color.*—Yellow-green 145C, with a point of russet in the center of each lenticel.
*Fruit lenticel diameter.*—0.3 mm.
*Fruit lenticel shape.*—Round near calyx end; increasingly elongated nearing stalk end.
*Fruit lenticel quantity.*—Many.
*Russet around stalk cavity.*—Absent.
*Russet on cheeks.*—Absent.
*Russet around eye basin.*—Absent.
*Length of stalk.*—43 mm.
*Diameter of stalk.*—1.8 mm.
*Stalk color.*—Red 53A.
*Depth of stalk cavity.*—18.8 mm.
*Width of stalk cavity.*—32 mm.
*Depth of eye basin.*—12.5 mm.
*Width of eye basin.*—32.1 mm.
*Diameter of eye.*—4 mm.
*Aperture of eye.*—Closed to slightly open.
*Length of sepal.*—6.8 mm.
*Firmness of flesh.*—5.6 kg/cm$^2$ after 4 months in storage.
*Flesh texture.*—Moderately crisp; somewhat granular.
*Flesh color.*—Red 50B closer to skin, about 30% of area; Yellow-orange 19D closer to center of fruit, about 70% of area.
*Number of locules.*—Average 5.1.
*Aperture of locules.*—Mostly open.
*Locule length.*—1.16 mm.
*Locule width.*—0.54 mm.
*Flavor and aroma.*—Balance acidity and sweetness; pleasant aroma.
*Juiciness.*—Very juicy.
*Brix.*—12.9° Brix after 4 months in storage.
Seeds:
*Quantity per fruit.*—Average 11.
*Length.*—8.5 mm.
*Width.*—4.7 mm.
*Shape.*—Elongated oval.
*Color.*—Greyed-purple 183A.
Harvest:
*Harvest date.*—Sep. 26, 2019; 7 days after 'Golden Delicious' (not patented).
*Number of picks.*—2.
Disease resistance/susceptibility: None noted.
Eating quality: Good to excellent.
Storageability: Up to about 4 months.
Market use: Fresh consumption.

The invention claimed is:

1. A new and distinct apple tree named 'R204' substantially as described and illustrated herein.

* * * * *